(12) United States Patent
Johnsen (10) Patent No.: US 9,867,689 B2
(45) Date of Patent: Jan. 16, 2018

(54) LOOP VASCULAR DEVICE AND METHOD TO RETRIEVE

(71) Applicant: Cook Medical Technologies, LLC, Bloomington, IN (US)

(72) Inventor: Jeppe Dufresne Johnsen, Froerup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 312 days.

(21) Appl. No.: 14/863,937

(22) Filed: Sep. 24, 2015

(65) Prior Publication Data

US 2016/0120635 A1    May 5, 2016

Related U.S. Application Data (60) Provisional application No. 62/073,155, filed on Oct. 31, 2014.

(51) Int. Cl.
*A61B 17/08*  (2006.01)
*A61F 2/01*  (2006.01)

(52) U.S. Cl.
CPC ........... *A61F 2/01* (2013.01); *A61F 2002/011* (2013.01); *A61F 2002/016* (2013.01); *A61F 2210/0004* (2013.01); *A61F 2220/0008* (2013.01); *A61F 2250/0023* (2013.01); *A61F 2250/0031* (2013.01); *A61F 2250/0043* (2013.01); *A61F 2250/0046* (2013.01); *A61F 2250/0054* (2013.01)

(58) Field of Classification Search
CPC ............ A61B 17/221; A61B 17/32056; A61B 2017/00358; A61B 2017/2212; A61B 2017/2215; A61F 2/01; A61F 2002/011; A61F 2002/016
See application file for complete search history.

(56) References Cited

U.S. PATENT DOCUMENTS

| | | |
|---|---|---|
| 6,620,183 B2 | 9/2003 | DiMatteo |
| 7,867,245 B2 | 1/2011 | Neeman et al. |
| 7,959,645 B2 | 6/2011 | WasDyke et al. |
| 8,273,099 B2 | 9/2012 | DiMatteo |
| 2001/0047169 A1* | 11/2001 | McGuckin, Jr. ........ A61B 10/02 606/45 |
| 2009/0254117 A1 | 10/2009 | Pakter |

* cited by examiner

*Primary Examiner* — Ashley Fishback
(74) *Attorney, Agent, or Firm* — Brinks Gilson & Lione (57) ABSTRACT

The present disclosure relates to a loop vascular device and a method to retrieve said device from the body vessel of a patient. The loop vascular device comprises a loop having a first portion extending distally to a first bar, and a second portion extending distally to a second bar. In a close state of the loop, the first and second bars are maintained or housed inside a first cannula. The first cannula may be in contact with a second cannula. Upon desiring to open the loop, the physician may separate the first cannula from the second cannula, allowing the bars to exit the first cannula and disconnect from each other, defining the open state of the loop. In the open state, the loop may be easily retrieved through any ingrowth in the body vessel.

20 Claims, 7 Drawing Sheets

LOOP VASCULAR DEVICE AND METHOD TO RETRIEVE

RELATED APPLICATIONS

This application claims the benefit of priority under 35 U.S.C. §119(a) to United States Provisional Application No. 62/073,155, filed on Oct. 31, 2014, which is incorporated by reference here in its entirety.

BACKGROUND

1. Technical Field

The present disclosure relates to medical devices. More particularly, the disclosure relates to a loop vascular device and method to retrieve said device from the body of a patient.

2. Background Information

Physicians often place medical devices within the vasculature to treat conditions such as pulmonary embolism, thrombosis, and aneurysm formation. Such devices may contain closed loop portions. One advantage of such closed loops is that they may exert low force on the vessel walls. In addition, such looped portions may contact the vessel walls and assist in device stabilization.

Over a period of time, device portions that contact the vessel wall may become endothelialized within the body vessel tissue. If the device is temporary, such endothelialization may make it difficult for the physician to remove these closed loop portions from the patient. There is a need for a closed loop device that is more easily retrieved after temporary placement, and a method to retrieve closed loop devices.

BRIEF SUMMARY

The present disclosure provides generally for a loop vascular device and apparatus to move the device. The disclosure also provides generally for a method to retrieve said loop device. The device may include a first portion having a first elongate body extending distally to a first bar, the first bar comprising a first proximal end and a first distal end. The device may further include a second portion having a second elongate body extending distally to a second bar, the second bar comprising a second proximal end and second distal end. The first proximal end may be in contact with the second proximal end to join the first and second portions.

The device may further include a first cannula disposed about the first elongate body and extending distally about the first and second bars to a first tubular end to maintain the first proximal end in contact with the second proximal end. The device may further include a second cannula disposed about the second elongate body and extending distally to a second tubular end. The second tubular end may be in contact with the first tubular end so that the first cannula maintains the first proximal end in contact with the second proximal end, defining a loop in a closed state.

Contrastingly, to define the loop in an open state, the first and second tubular ends may be slidable so that the first cannula distally extends up to only proximal to the second distal end to allow the first proximal end to separate from the second proximal end. In one embodiment, the second cannula distally extends up to only proximal to the first distal end in the open state to allow the first proximal end to separate from the second proximal end.

Additionally, the first and second cannulas may comprise a polymer material. The first elongate member may be a first wire and the second elongate member may be a second wire. Both may be tubular members. Either of the first or second wires may comprise Nitinol.

In an alternative embodiment, the first and second bars may be L-shaped. The first bar may include a first protrusion and the second bar may include a second protrusion to form the L-shape. The device may comprise a plurality of loops, such that any of the features described herein applies to each loop in the plurality.

Said loop device has as one advantage that it may be easily removed if the device has been endothelialized by converting the closed loop into an open loop. The open loop has features similar to a pair of substantially straight struts. Therefore, the open loop may be fed through the endothelialized tissue reducing or eliminating any potential negative effects on the vessel wall. Preferably, no portion of the device remains in the body vessel after retrieval.

A method for retrieving the device described herein may include (1) disposing the device within the body vessel and (2) disconnecting the first bar from the second bar to split the first portion from the second portion in the body vessel. The method may also include retrieving the device from the body vessel. The step of disconnecting may comprise applying a first force in a first direction to the first cannula and a second force in a second direction to the second cannula to separate or split the first tubular end from the second tubular end.

The step of applying the first and second forces may comprise the first direction being opposite from the second direction. In one embodiment, the step of applying the first and second forces comprises the first and second directions being substantially perpendicular to the longitudinal axis. In one embodiment, the step of applying the first and second forces comprises the first and second forces being less than 100 Newtons each. More preferably, the step of applying the first and second forces comprises the first and second forces being about 5 Newtons to about 20 Newtons each.

The step of disconnecting the first bar from the second bar may include removing the first and second bars from the first cannula after the step of applying. The step of disconnecting the first bar from the second bar may also include allowing the first proximal end to separate from the second proximal end after the step of removing the bars to open the loop.

The step of retrieving may comprise retrieving through a femoral access point or a jugular access point, whichever is preferred. The step of retrieving may include retrieving the entire device from the body vessel. Just as with the device, the step of disposing may include the loop being a plurality of loops.

DETAILED DESCRIPTION OF THE DRAWINGS

The present disclosure provides for a loop vascular device and method to retrieve said loop device. The materials, methods, and examples disclosed herein are illustrative only and not intended to be limiting. The disclosed figures are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which this disclosure pertains. In case of conflict, the present document and definitions will control.

"Adjacent" referred to herein is nearby, near to, or in close proximity with.

The terms "proximal" and "distal" and derivatives thereof will be understood in the frame of reference of a medical physician using the device. Thus, proximal refers to locations closer to the physician and distal refers to locations further away from the physician (e.g. deeper in the patient's vascular).

"Substantially" or derivatives thereof will be understood to mean significantly or in large part.

Figure 1A:
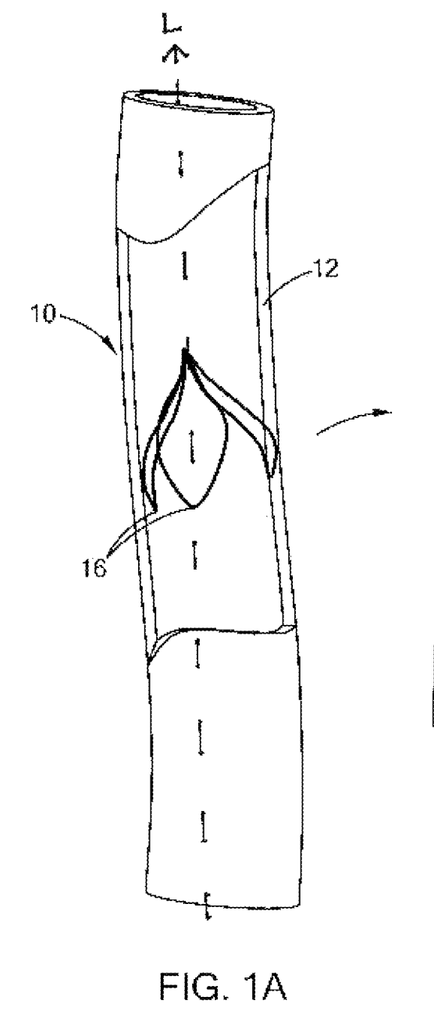
FIGS. 1A-B are environmental, side views of a medical device for treatment in a body vessel in accordance with one embodiment of the present invention.
Figure 1B:
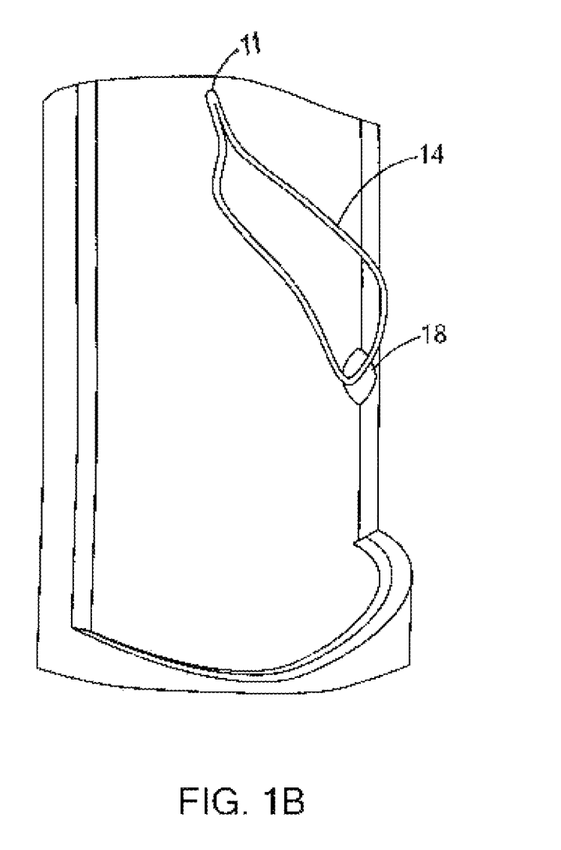

FIGS. 1A-B illustrate loop device 10 within the body vessel. In FIG. 1A, the body vessel has a vessel wall 12. The device 10 comprises loops having apices 16 contacting vessel wall 12. This view also depicts the body vessel having a longitudinal axis, L. In a blown-up, partial view of FIG. 1A, FIG. 1B shows an isolated loop 14 of the device 10. One of skill in the art will understand that loop 14 may be representative of all loops in the device 10. Loop 14 has been ingrown or endothelialized into the vessel wall 12 with ingrowth 18. Ingrowth 18 has covered a portion of loop 14. Ingrowth 18 may assist in stabilizing device 10 within the body vessel during treatment. In addition, the device has a tip 11. Each loop 14 may be attached at the tip 11.

Figure 2A:
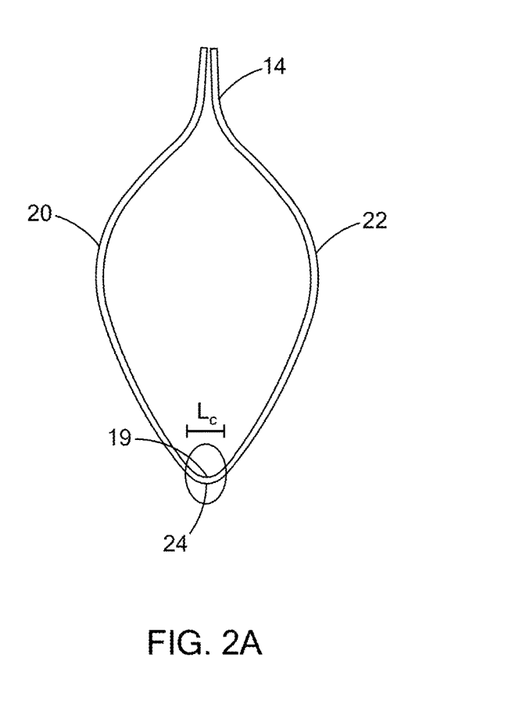
FIGS. 2A-B are side views of a loop of the device of FIG. 1A.
Figure 2B:
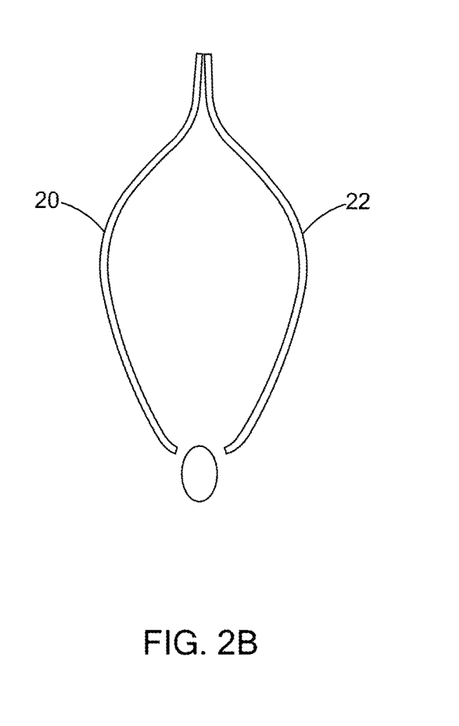

After treatment, the physician may desire to remove device 10 from the body vessel. FIGS. 2A-B illustrate the closed state and the open state of loop 14, respectively. In FIG. 2A, loop 14 comprises a first portion 20 extending distally to a distal portion 24 and a second portion 22 extending distally to the distal portion 24, defining the loop 14 in the closed state. The device may comprise contact portion 19 that contacts the vessel wall and has a contact length $L_C$. Such contact length may become endothelialized with ingrowth. In FIG. 2B, to retrieve the device the first portion 20 disconnects or separates from the second portion 22, defining the loop 14 in an open state. The open state may assist in device removal after treatment.

Figure 3A:
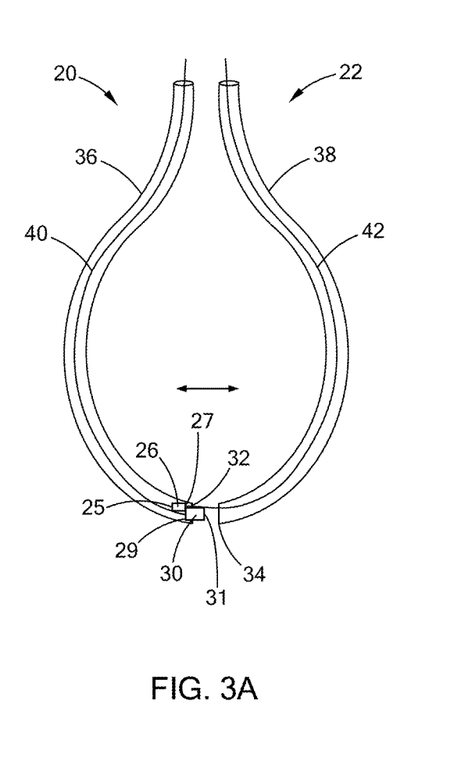
FIGS. 3A-B are partial, side views of a loop of FIG. 1A.
Figure 3B:
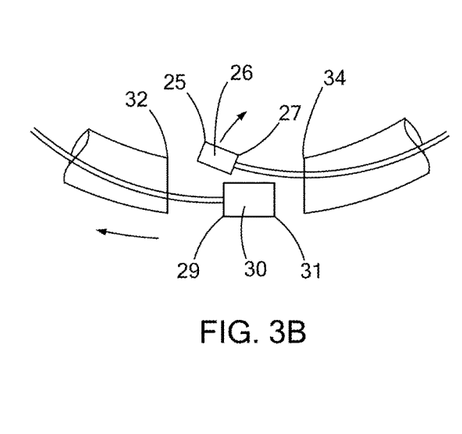

FIGS. 3A-B illustrate one embodiment of the loop. In this embodiment, the first portion 20 comprises a first elongate body 40 extending distally to a first bar 30. The first bar 30 comprises a first proximal end 29 and a first distal end 31. Further, the second portion comprises a second elongate body 42 extending distally to a second bar 26. The second bar comprises a second proximal end 27 and a second distal end 25. As shown in FIG. 3A, the second proximal end 27 may be in contact with the first proximal end 29 to join the first and second portions (20 and 22, respectively). The first bar 30 may be the same size and shape as the second bar 26.

The first and second elongate bodies may be formed of any material known in the art. They may have a sufficient flexibility to navigate through the vasculature, while maintaining an appropriate stiffness to hold the loop in place when in the body vessel. In one embodiment, the first elongate member 40 is a first wire and the second elongate member 42 is a second wire. The first and second wires may comprise Nitinol.

Nitinol is a metal alloy of nickel and titanium having unique shape memory setting properties and being biocompatible. At a transition temperature, Nitinol may undergo a phase change from Martensite to Austenite, changing its structure. In addition to this phase change ability, Nitinol is also quite flexible.

The device may further comprise a first cannula 36 disposed about the first elongate body 40. The first cannula 36 may extend distally about the first and second bars (30 and 26, respectively) to a first tubular end 32 to maintain the first proximal end 29 in contact with the second proximal end 27. The first cannula 36 may extend over the first and second bars to maintain them in contact in the closed state of the loop.

The device may further comprise a second cannula 38 disposed about the second elongate body 42. The second cannula 38 may extend distally to a second tubular end 34. The second tubular end 34 may be in contact with the first tubular end 32 so that the first cannula 36 maintains the first proximal end 29 in contact with the second proximal end 27, defining the loop in a closed state.

The first tubular end 32 and the second tubular end 34 may be slidable so that the first cannula 36 extends up to only proximal to the second distal end 25 to allow the first proximal end 29 to separate from the second proximal end 27, defining the loop in an open state. In other words, when the loop is in the closed state, the first proximal end 29 and the second proximal end 27 may be in contact. However, when the physician desires to open the loop, the physician may move the first cannula 36 in the direction of the arrows (shown in FIG. 3A) to move the first tubular end 32 past or proximal to the second distal end 25. This movement allows the first and second bars to separate from each other to disconnect the first portion 20 from the second portion 22.

To facilitate disconnecting, the second cannula 38 may extend up to only proximal to the first distal end 31 to allow the first proximal end 29 to separate from the second proximal end 27 in the open state. In other words, to the extent that any part of the bars is disposed in the second cannula 38, the second cannula 38 may slide or move to remove the bars from the cannulas, in the direction of the arrows (shown in FIG. 3A). The physician may separate the first tubular end 32 from the second tubular end 34 by applying force to the cannulas to split the first portion 20 from the second portion 22.

Although the cannulas are slidable, they may be attached to the device. In one embodiment, the cannulas are attached or secured at or adjacent to the tip. One skilled in the art will appreciate that this attachment may limit the slidability of the cannulas over the elongate members. In one embodiment, the first cannula 36 extends up to only proximal and adjacent to the second distal end 25. In addition, the second cannula extends up to only proximal and adjacent to the first distal end 31.

FIG. 3B depicts a blown-up view of the first and second bars upon separating the first portion 20 from the second portion 22. In this embodiment, the physician may apply a force or pull on the first cannula in the direction of the arrow to disconnect or split the first cannula from the second cannula. The physician may apply a first force in a first direction to the first cannula.

In addition, the physician may apply a second force in a second direction to the second cannula to separate the first tubular end 32 from the second tubular end 34. Upon disconnecting the first and second tubular ends, the first and second bars (30 and 26, respectively) may move out of the cannulas. Upon exiting the cannulas, the first proximal end 29 may disconnect from the second proximal end 27, as shown with the arrows in FIG. 3B. This moves the loop from the closed state to the open state.

Figure 4:
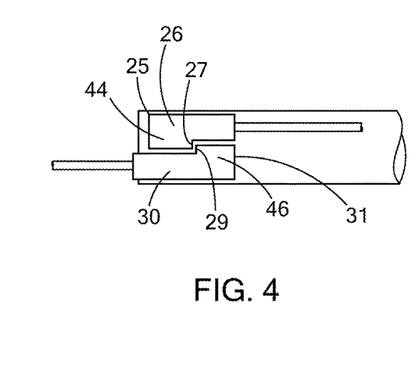
FIG. 4 is a partial, side view of a loop of FIG. 1A.

FIG. 4 illustrates another embodiment of the first and second bars (30 and 26, respectively). In this embodiment, the first and second bars may be L-shaped. The first bar 30 may comprise a first protrusion 46 adjacent to the first distal end 31 to form the L-shape. Further, the second bar 26 may comprise a second protrusion 44 adjacent to the second distal end 25 to form the L-shape. The two opposing L-shapes may fit together inside of the cannulas. In this embodiment, the second proximal end 27 is in contact with the first proximal end 29 in the closed state.

Figure 5A:
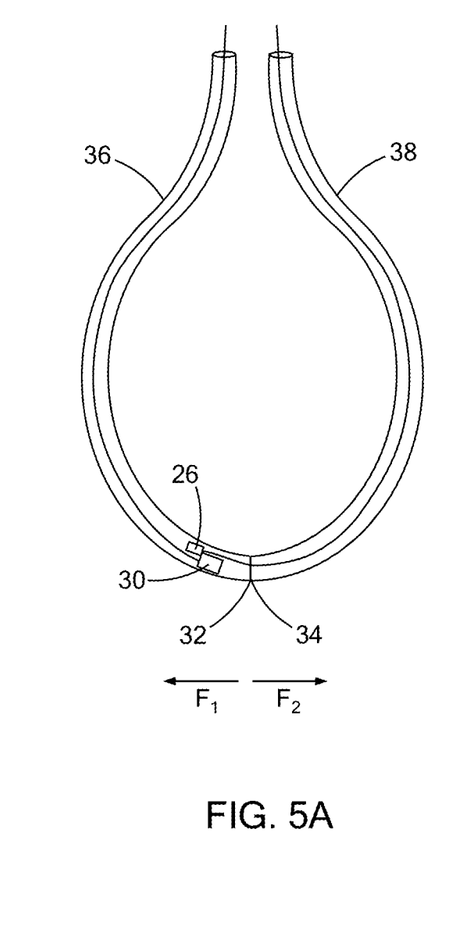
FIGS. 5A-B are partial, side views of a closed state and an open state of the loop of FIG. 1A.
Figure 5B:
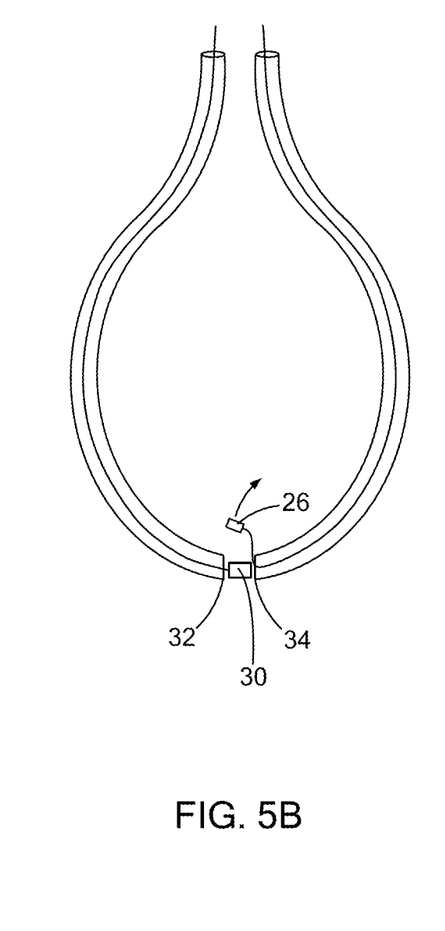

FIGS. 5A-B depict the closed state and open state, respectively, in further detail. In FIG. 5A, the device may be disposed inside the body vessel. The first bar 30 and the second bar 26 are disposed inside of the first cannula 36. In this state, the first tubular end 32 is in contact with the second tubular end 34. When the physician desires to open the loop he or she may apply a force to separate the first tubular end 32 from the second tubular end 34.

This may be a first force $F_1$ in a first direction to the first cannula 36. It may also be a second force $F_2$ in a second direction to the second cannula 38. In this embodiment, the first and second forces ($F_1$ and $F_2$, respectively) may be in a first direction being opposite from the second direction, as depicted in the arrows in FIG. 5A. The first and second directions may be substantially perpendicular to the longitudinal axis. In one embodiment, the first and second forces are less than 100 Newtons each. The first and second forces may be about five Newtons to about 20 Newtons each.

In FIG. 5B, after applying the forces, the first tubular end 32 may separate from the second tubular end 34. This allows the first bar 30 to move outside of the first cannula 36 and disconnect from the second bar 26. The second bar 26 moves or pops out of the first cannula 36 in the direction of the arrow in FIG. 5B. This defines the loop in an open state.

While the physician may apply a force to split the first portion from the second portion, one skilled in the art will understand that other methods to separate the first tubular end 32 from the second tubular end 34 could be employed. For example, a part of the device could biodegrade or otherwise be removed to facilitate separating the bars. In addition, one skilled in the art will understand that while these features have been discussed with reference to one loop, the loop could be a plurality of loops. Each loop of the plurality of loops could have the structures and features discussed herein. In one embodiment, the loop is four loops.

Additionally, the bars could be attached to the elongate members through any means known in the art, including gluing, soldering, welding, or bonding the portions together. The first and second tubular ends may connect at or adjacent to the apex of each loop. However, the first and second tubular ends may connect anywhere that the physician desires the loop to split.

Figure 6A:
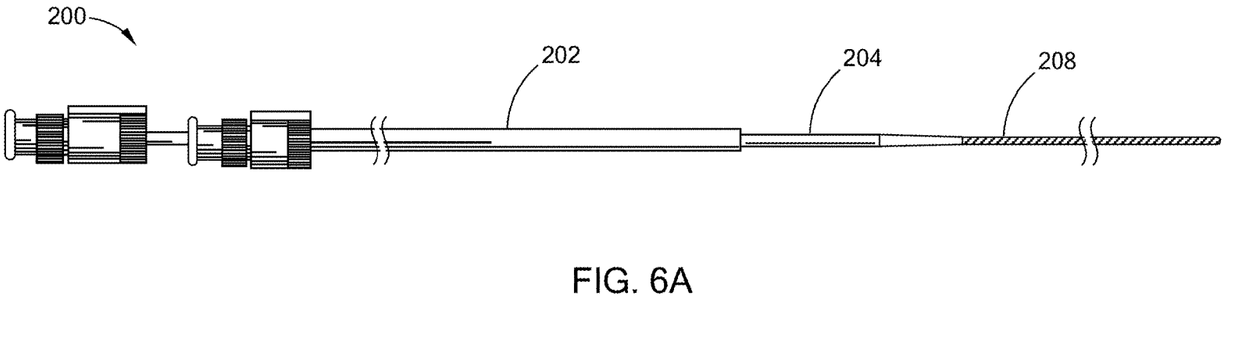
FIGS. 6A-B show a delivery assembly for introducing the device of FIG. 1A in accordance with one embodiment of the present invention.
Figure 6B:
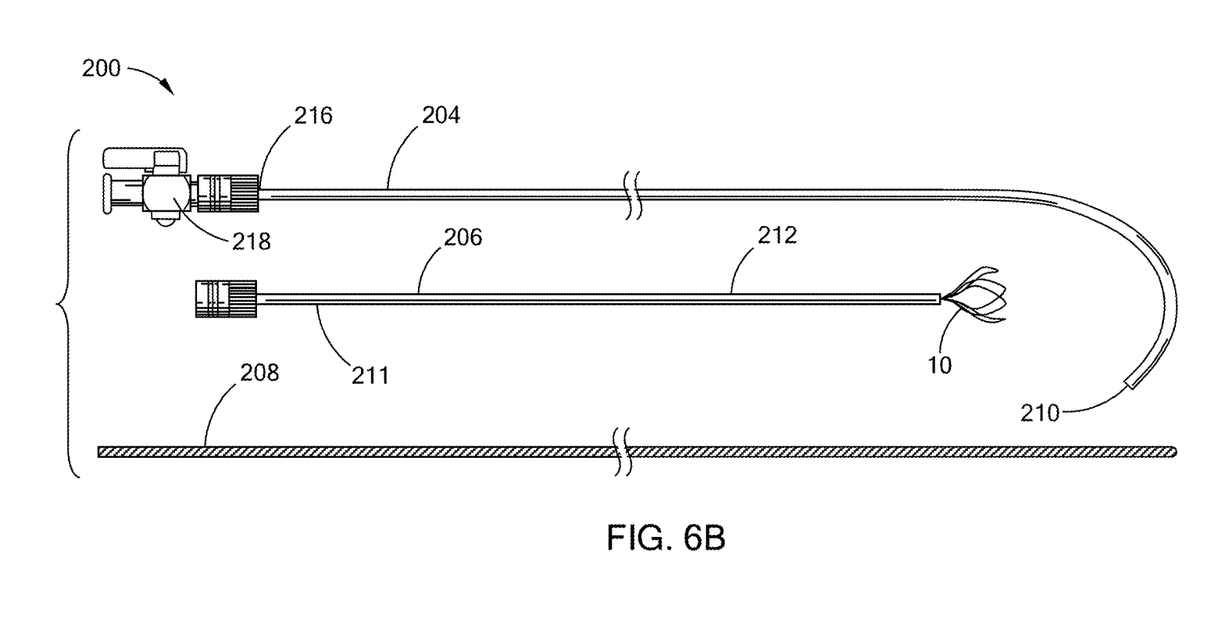

FIGS. 6A-B illustrates a delivery or retrieval apparatus for introducing or retrieving the device discussed herein. The device may be delivered or retrieved by way of the Seldinger technique. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner member or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

When performing the Seldinger technique, a needle may also be used. The needle may be used for percutaneously introducing the wire guide into the patient's body through an access site. A cutting device may also be used to expand the access site.

The device may be delivered by way of an inner sheath or catheter, being removably coupled to the inner catheter by way of a coupling member. In one embodiment, when the distal end 210 of the outer sheath 204 is at the desired location in the body vessel, the wire guide 208 is removed. Then device 10, having a proximal segment contacting a distal portion 212 of the inner catheter 206, is inserted into the outer sheath 204. The inner catheter 206 is advanced through the outer sheath 204 for deployment of the device 10 through the distal end 210 to treat the body vessel. The catheter 206 extends from a proximal portion 211 to a distal portion 212 and is configured for axial movement relative to the outer sheath 204. In this example, the distal portion 212 is shown adjacent to the device 10. Thus, before deployment, the device 10 is coaxially disposed within the lumen of the outer sheath 204 and removably coupled to the distal portion 212 of the catheter 206, or in the alternative, the device 10 is merely pushed by, but not coupled to, the distal portion 212 of the catheter 206.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner catheter 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end 210 of the outer sheath 204 adjacent the deployed device 10 in the vasculature. The inner catheter 206 is advanced through the outer sheath 204 until the distal portion 212 protrudes from the distal end 210 of the outer sheath 204. The distal portion 212 is coupled to a proximal end of the device 10, after which the inner catheter 206 is retracted proximally, drawing the device 10 into the outer sheath 204.

The device 10 may have a collapsed state for delivery and an expanded state for retrieval. For example, the collapsed state may have a smaller profile to fit inside the delivery apparatus. The device 10 may expand upon exiting the delivery apparatus, as shown in FIG. 6B. In addition, a skilled artisan will understand that the delivery or retrieval apparatus may be modified with feature to perform the desired splitting technique discussed herein. For example, the distal portion 212 may be modified to apply the forces shown and discussed in the above figures.

It is understood that the assembly described above is merely one example of an assembly that may be used to deploy the device in a body vessel. Of course, other apparatus, assemblies and systems may be used to deploy any embodiment of the device without falling beyond the scope or spirit of the present invention.

Figure 7:
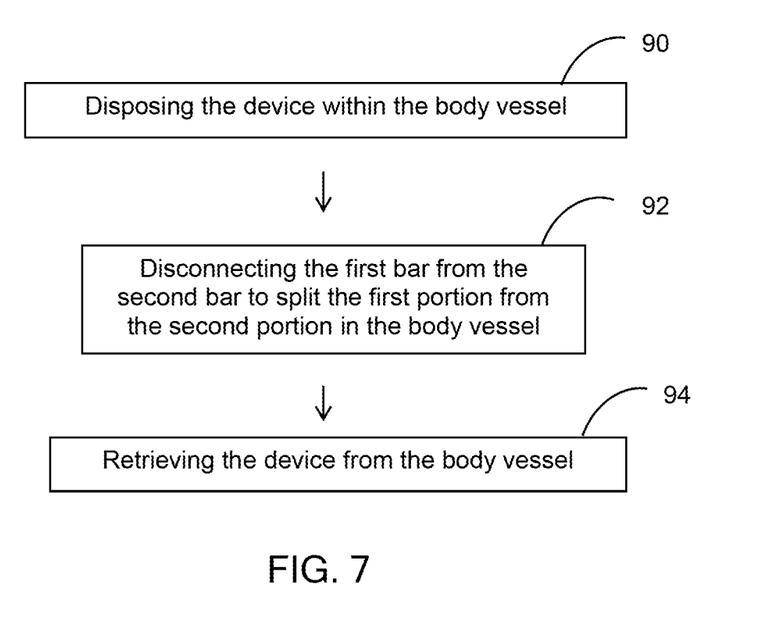
FIG. 7 is a flow diagram of one method of retrieving the device of FIG. 1A from the body vessel in accordance with one example of the present invention.

FIG. 7 depicts a flow diagram of one method to retrieve the device discussed herein. In step 90, the physician may dispose the device within the body vessel. In step 92, the physician may disconnect the first bar from the second bar to split the first portion from the second portion in the body vessel using any method described herein. In step 94, the physician may retrieve the device from the body vessel.

As discussed herein, the step of disconnecting may comprise applying a first force in a first direction to the first cannula and a second force in a second direction to the second cannula to disconnect the first tubular end from the second tubular end. The step of disconnecting may also involve removing the first and second bars from the first cannula after the step of applying (as shown in FIGS. 5A-B). Additionally, the method may include allowing the first proximal end to separate from the second proximal end after the step of removing the bars to open the loop and before the step of disconnecting the first and second bars (also shown in FIGS. 5A-B).

Figure 8A:
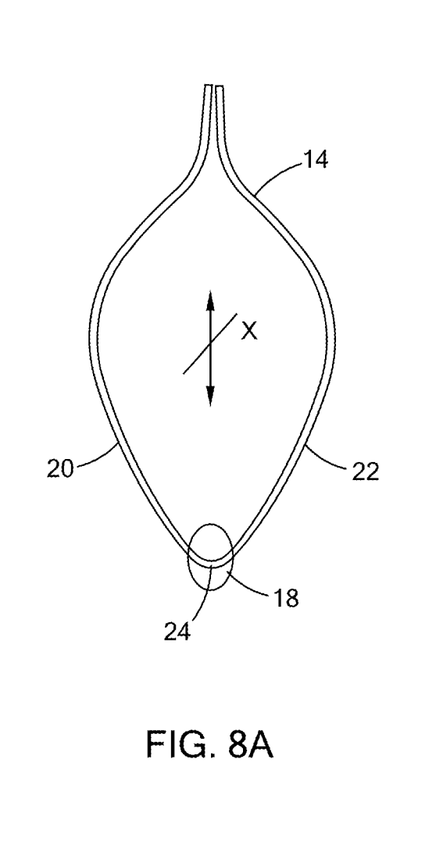
FIGS. 8A-C depict the steps of the method of FIG. 7.
Figure 8B:
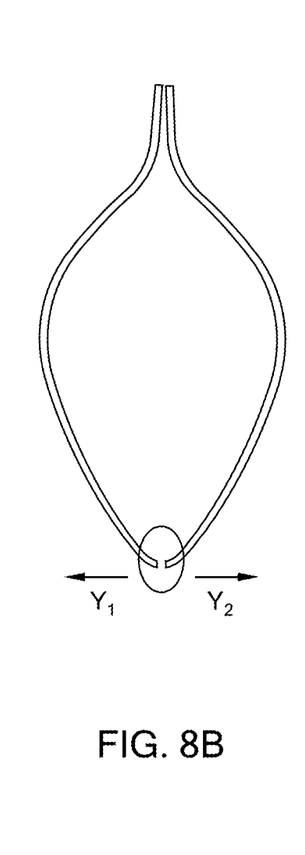

FIGS. 8A-C depict drawings of the method steps in FIG. 7. The bars are not shown here for simplicity. However, it will be understood that the bars would operate as described in the foregoing figures. In FIG. 8A, the loop 14 may have ingrowth 18, securing the loop 14 to the vessel wall. Because of the ingrowth 18, the loop 14 may not be able to move in the direction of arrow X. The physician may disconnect the first portion 20 from the second portion 22 in the direction of arrows Y1 and Y2 by applying a force to separate the first tubular end from the second tubular end. Once the force has been applied, the bars may be removed from the cannulas. After the bars are removed from the cannulas, the bars may disconnect to convert the loop into the open state, as in FIG. 8B and discussed herein.

Figure 8C:
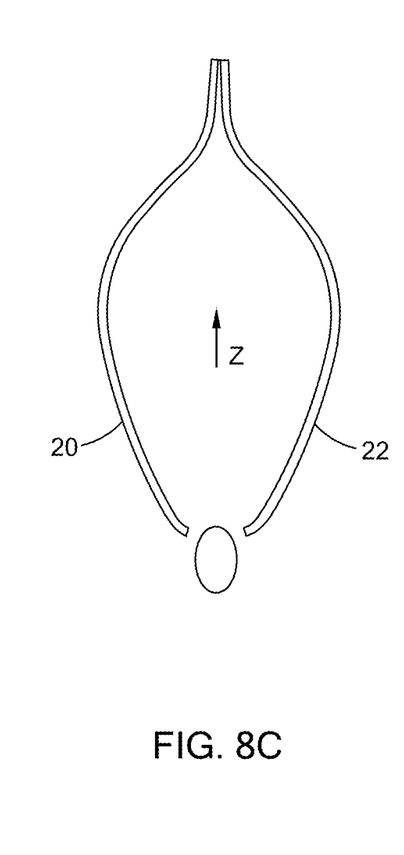

In FIG. 8C, the first portion 20 is split from the second portion 22. The first and second portions may form substantially straight struts, which may be retrieved or pulled through ingrowth 18 in the direction of arrow Z, reducing or eliminating possible negative effects upon retrieval.

The step of retrieving may further comprise retrieving through a femoral access point or a jugular access point. A skilled artisan will understand that a physician may use either a femoral access point or a jugular access point to perform the Seldinger technique. In addition, the step of retrieving may comprise retrieving the entire device from the body vessel such that no part of the device remains in the body vessel after retrieval. All parts of the device are removed by either femoral or jugular access. The steps performed on the loop depicted may be performed on each loop of a plurality of loops in the device.

While the present invention has been described in terms of certain preferred embodiments, it will be understood that the invention is not limited to these disclosed embodiments as those having skill in the art may make various modifications without departing from the scope of the following claims.

The invention claimed is:

1. A device for treatment in a body vessel, the device comprising:
   a first portion comprising a first elongate body extending distally to a first bar, the first bar comprising a first proximal end and a first distal end;
   a second portion comprising a second elongate body extending distally to a second bar, the second bar comprising a second proximal end and second distal end, the first proximal end being in contact with the second proximal end to join the first and second portions;
   a first cannula disposed about the first elongate body and extending distally about the first and second bars to a first tubular end to maintain the first proximal end in contact with the second proximal end;
   a second cannula disposed about the second elongate body and extending distally to a second tubular end, the second tubular end being in contact with the first tubular end so that the first cannula maintains the first proximal end in contact with the second proximal end, defining a loop in a closed state; and
   the first and second tubular ends being slidable so that the first cannula distally extends up to only proximal to the second distal end, defining the loop in an open state, to allow the first proximal end to separate from the second proximal end.

2. The device of claim 1 wherein the second cannula distally extends up to only proximal to the first distal end in the open state to allow the first proximal end to separate from the second proximal end.

3. The device of claim 1 wherein the first elongate member is a first wire and the second elongate member is a second wire.

4. The device of claim 1 wherein the first and second elongate members are tubular.

5. The device of claim 1 further comprising a tip wherein the first and second cannulas are attached at the tip.

6. The device of claim 1 wherein the first and second bars are L-shaped.

7. The device of claim 6 wherein the first bar comprises a first protrusion and the second bar comprises a second protrusion to form the L-shape.

8. The device of claim 1 wherein the device comprises a plurality of loops, each loop having the first and second portions.

9. A method for retrieving a device from a body vessel, the body vessel having a longitudinal axis, the method comprising:

disposing the device within the body vessel, the device comprising:
a first portion comprising a first elongate body extending distally to a first bar, the first bar comprising a first proximal end and a first distal end;
a second portion comprising a second elongate body extending distally to a second bar, the second bar comprising a second proximal end and second distal end, the first proximal end being in contact with the second proximal end to join the first and second portions;
a first cannula disposed about the first elongate body and extending distally about the first and second bars to a first tubular end to maintain the first proximal end in contact with the second proximal end;
a second cannula disposed about the second elongate body and extending distally to a second tubular end, the second tubular end being in contact with the first tubular end so that the first cannula maintains the first proximal end in contact with the second proximal end, defining a loop in a closed state; and
the first and second tubular ends being slidable so that the first cannula distally extends up to only proximal to the second distal end to allow the first proximal end to separate from the second proximal end, defining the loop in an open state; and disconnecting the first bar from the second bar to separate the first portion from the second portion in the body vessel.

10. The method of claim 9 wherein the step of disconnecting the first bar from the second bar comprises applying a first force in a first direction to the first cannula and a second force in a second direction to the second cannula to separate the first tubular end from the second tubular end.

11. The method of claim 10 wherein the step of applying the first and second forces comprises having the first direction being opposite from the second direction.

12. The method of claim 11 wherein the step of having the first direction being opposite from the second direction comprises having the first and second directions being substantially perpendicular to the longitudinal axis.

13. The method of claim 10 wherein the step of applying the first and second forces comprises having the first and second forces being less than 100 Newtons each.

14. The method of claim 9 further comprising removing the first and second bars from the first cannula after the step of disposing the device and before the step of disconnecting the first bar from the second bar.

15. The method of claim 14 further comprising the step of allowing the first proximal end to separate from the second proximal end after the step of removing the bars and before the step of disconnecting the first bar from the second bar.

16. The method of claim 9 further comprising retrieving the device from the body vessel after the step of disconnecting the first bar from the second bar.

17. The method of claim 16 wherein the step of retrieving the device comprises retrieving through a femoral access point or a jugular access point.

18. The method of claim 16 wherein the step of retrieving the device comprises retrieving the entire device from the body vessel.

19. The method of claim 9 wherein the step of disposing the device comprises having the device comprising a plurality of loops, each loop having one first portion and one second portion.

20. An apparatus comprising:
an inner sheath;
a coupling member; and
a device removably coupled to the inner sheath by way of the coupling member, the device comprising:
a first portion comprising a first elongate body extending distally to a first bar, the first bar comprising a first proximal end and a first distal end;
a second portion comprising a second elongate body extending distally to a second bar, the second bar comprising a second proximal end and second distal end, the first proximal end being in contact with the second proximal end to join the first and second portions;
a first cannula disposed about the first elongate body and extending distally about the first and second bars to a first tubular end to maintain the first proximal end in contact with the second proximal end;
a second cannula disposed about the second elongate body and extending distally to a second tubular end, the second tubular end being in contact with the first tubular end so that the first cannula maintains the first proximal end in contact with the second proximal end, defining a loop in a closed state; and
the first and second tubular ends being slidable so that the first cannula distally extends up to only proximal to the second distal end, defining the loop in an open state, to allow the first proximal end to separate from the second proximal end.

* * * * *